United States Patent [19]

Hasselberg et al.

[11] Patent Number: 5,286,450
[45] Date of Patent: Feb. 15, 1994

[54] BILIRUBIN ASSAY USING CROSSLINKABLE POLYMERS

[75] Inventors: Stephen C. Hasselberg, Rochester; Ignazio S. Ponticello, Pittsford; David M. Taylor, Rochester, all of N.Y.

[73] Assignee: Eastman Kodak Company, Rochester, N.Y.

[21] Appl. No.: 892,073

[22] Filed: Jun. 1, 1992

[51] Int. Cl.$^5$ .................... G01N 21/77; G01N 33/00
[52] U.S. Cl. .......................... 422/56; 422/57; 436/97; 436/169; 436/170; 436/175
[58] Field of Search ............... 422/56, 57, 58; 436/97, 436/169, 170, 175

[56] References Cited

U.S. PATENT DOCUMENTS

| | | | |
|---|---|---|---|
| H600 | 3/1989 | Tanaka et al. | 422/56 |
| 2,085,581 | 6/1937 | Green | 137/65 |
| 3,106,468 | 10/1963 | Burness | 430/623 |
| 3,232,764 | 2/1966 | Allen et al. | 430/420 |
| 3,325,387 | 6/1967 | Yamamoto et al. | 430/543 |
| 3,459,790 | 8/1969 | Smith | 560/178 |
| 3,490,911 | 1/1970 | Burness et al. | 430/543 |
| 3,539,644 | 11/1970 | Burness et al. | 568/32 |
| 3,542,558 | 11/1970 | Burness et al. | 430/623 |
| 3,554,987 | 1/1971 | Smith | 526/240 |
| 3,575,705 | 4/1971 | Nakajima et al. | 430/377 |
| 3,640,720 | 2/1972 | Cohen | 430/622 |
| 3,841,872 | 10/1974 | Burness et al. | 430/415 |
| 3,904,418 | 9/1975 | Mowrey et al. | 430/217 |
| 3,929,482 | 12/1975 | Ponticello et al. | 430/627 |
| 3,939,130 | 2/1976 | Ponticello | 528/220 |
| 3,957,882 | 5/1976 | Silverman et al. | 568/35 |
| 3,992,158 | 11/1976 | Przybylowicz et al. | 422/57 |
| 4,017,442 | 4/1977 | Gibbs et al. | 524/460 |
| 4,069,016 | 1/1978 | Wu | 436/97 |
| 4,069,017 | 1/1978 | Wu et al. | 436/97 |
| 4,161,407 | 7/1979 | Campbell | 430/621 |
| 4,215,195 | 7/1980 | Ponticello et al. | 430/496 |
| 4,247,673 | 1/1981 | Ponticello et al. | 526/263 |
| 4,258,001 | 3/1981 | Pierce et al. | 422/56 |
| 4,288,531 | 9/1981 | Adin et al. | 430/338 |
| 4,292,272 | 9/1981 | Kitajima et al. | 422/57 |
| 4,303,408 | 12/1981 | Kim et al. | 422/56 X |
| 4,311,665 | 1/1982 | Wu | 436/97 X |
| 4,333,733 | 6/1982 | Sanford et al. | 422/56 X |
| 4,338,095 | 7/1982 | Wu | 436/97 |
| 4,346,231 | 8/1982 | Ponticello et al. | 560/178 |
| 4,412,005 | 10/1983 | Wu | 436/97 |
| 4,430,436 | 2/1984 | Koyama et al. | 436/531 |
| 4,438,278 | 3/1984 | Ponticello et al. | 560/205 |
| 4,472,498 | 9/1984 | Masuda et al. | 422/56 X |
| 4,548,870 | 10/1985 | Ogawa et al. | 428/474.7 |
| 4,548,905 | 10/1985 | Wu | 436/97 |
| 4,637,978 | 1/1987 | Dappen | 435/11 |
| 4,781,890 | 11/1988 | Arai et al. | 422/56 |
| 4,788,153 | 11/1988 | Detwiler et al. | 436/97 |
| 4,868,106 | 9/1989 | Ito et al. | 422/56 X |
| 4,877,579 | 10/1989 | Yazawa et al. | 436/97 X |
| 4,895,704 | 1/1990 | Arai et al. | 422/56 X |
| 4,948,480 | 8/1990 | Christy, Jr. et al. | 204/182.8 |

FOREIGN PATENT DOCUMENTS 57-101760 6/1982 Japan .

Primary Examiner—James C. Housel
Assistant Examiner—Maureen M. Wallenhorst
Attorney, Agent, or Firm—John R. Everett

[57] ABSTRACT

A colorimetric assay for the determination of conjugated or unconjugated bilirubin in biological fluids can be carried out with an improved analytical element. The element includes a support having thereon a gelatin-free mordant layer with a positively-charged interactive mordant having at least one binding site for bilirubin, a radiation-blocking layer, and a porous spreading layer. The interactive mordant is dispersed in a binder material of crosslinkable copolymers which include a monomer capable of reaction with a crosslinking agent to crosslink the copolymer.

8 Claims, No Drawings

BILIRUBIN ASSAY USING CROSSLINKABLE POLYMERS

FIELD OF THE INVENTION

This invention relates to an assay for conjugated or unconjugated bilirubin in clinical chemistry. It also relates to a dry analytical element useful in this assay and to certain polymers which are particularly useful as binder material in the element.

BACKGROUND OF THE INVENTION

Bilirubin is a degradation product of hemoglobin. In a healthy individual, bilirubin released from aged or damaged red blood cells in the body is excreted or degraded into other derivatives. In some cases, however, an abnormal amount of bilirubin occurs within the body in the case of excessive hemolysis or liver failure. There is evidence that excessive amounts of bilirubin in the blood can lead to an undesirable increase in bilirubin concentration within the body cells which interferes with various cellular processes. The clinical significance of bilirubin determination, then, in tests for liver and other related organ functions, is apparent.

In human body fluids such as bile and serum, bilirubin exists in several different forms, these forms commonly being referred to in the art as conjugated bilirubin ($B_c$, both mono- and diconjugated forms), unconjugated bilirubin ($B_u$, also known as indirect bilirubin), and delta bilirubin (also known as biliprotein). The total bilirubin content ($B_T$), represents the sum of all forms of bilirubin.

A variety of colorimetric assays for bilirubin are known. For example, U.S. Pat. No. 4,069,017 describes an assay for bilirubin carried out on a dry multilayer analytical element containing an interactive mordant in a reagent layer which binds to bilirubin thereby producing a detectable product. The mordant also enhances the molar absorptivity of bilirubin and causes a spectral shift in the unconjugated moiety making possible the simultaneous analysis of both conjugated and unconjugated bilirubin by reading reflectance density at 400 and 460 nm. The element also comprises a porous spreading layer and a radiation-blocking layer. Chromophores which can cause spectral interference, such as hemoglobin and delta bilirubin, are retained in the spreading layer above the radiation blocking layer. The bilirubin species, Bu and Bc, migrate through the radiation blocking layer to bind with the mordant. The interactive mordant is dispersed in a binder material such as gelatin or its derivatives.

Unfortunately, gelatin and its derivatives have a slight color change over time in the 400 to 460 nm region of the spectrum, making for poor stability of the system.

A significant advance in the art is described in U.S. Pat. No. 4,788,153 (issued Nov. 29, 1988 to Detwiler). The assay for bilirubin described therein is carried out on an analytical element substantially free of gelatin in the reagent layer. An alternative polymer, poly(acrylamide-co-N-vinylpyrrolidone), was used as the reagent layer vehicle.

However, this polymer is not crosslinkable and the structural integrity of the element cannot be maintained during the analysis, resulting in interferences due to hemoglobin and deltabilirubin.

It is therefore desirable to obtain for use in the reagent layer binder materials that do not absorb light in the 400 to 460 nm range of the spectrum, and which maintain structural integrity.

SUMMARY OF THE INVENTION

The problems described above have been solved with an analytical element for the determination of conjugated or unconjugated bilirubin comprising a support having thereon, in order:

(A) a reagent layer comprising a positively-charged interactive mordant for bilirubin, said mordant being dispersed in a binder material which is a copolymer derived from:
  (1) one or more monomers selected from the group consisting of acrylamide and N-vinylpyrrolidinone; and
  (2) one or more crosslinkable monomers selected from the group consisting of (i) primary amino group-containing monomers, (ii) active methylene group-containing monomers, and (iii) activated halogen group-containing monomers;
(B) a radiation blocking layer; and
(C) a porous spreading layer.

This invention also provides a method for the determination of conjugated or unconjugated bilirubin in an aqueous liquid comprising the steps of:

(A) contacting the aqueous liquid with the above-described analytical element; and
(B) measuring the amount of conjugated or unconjugated bilirubin bound to said interactive mordant.

The element of this invention can be used in an assay for either conjugated or unconjugated bilirubin. Because of the crosslinkable polymer vehicle in the reagent layer, it is less susceptible to deterioration than prior art elements. Certain of these polymers are hydrolytically stable and thus the crosslinking will remain intact and maintain coating integrity. The element of the invention demonstrates better stability and less interference from serum pigments such as hemoglobin.

It was surprising to find that incorporation of certain monomers capable of being crosslinked with common hardeners could produce polymeric binder materials showing such significant improvements. These results were unexpected because crosslinking affects diffusion in and out of the reagent layer and therefore would be expected to have deleterious effects on the diffusion of reagents in the element As explained below, it is important that all reagents in the element be in fluid contact.

Further, some monomers of the invention have reactive methylene groups which, under high pH conditions, would be expected to form condensation products leading to yellow color interferents. Surprisingly, color interference did not occur.

DETAILED DESCRIPTION OF THE INVENTION

The present invention relates to the determination of bilirubin (conjugated or unconjugated) in aqueous liquids. In particular, the invention can be used to assay biological fluids of either animals or humans, but preferably of humans. Such fluids include, but are not limited to, whole blood, plasma, serum, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like.

The method of this invention can be practiced with a dry multilayer analytical element comprising a support having thereon a multiplicity of individual layers. The uppermost layer is a spreading layer to uniformly distribute the aqueous liquid over the element. Serum proteins and other pigments such as hemoglobin remain in the spreading layer on the basis of molecular size. A radiation-blocking layer, directly beneath the spreading layer, allows the diffusion of bilirubin to the reagent layer underneath, but blocks light from the pigments retained in the spreading layer. The bottom layer contains a mordant to bind bilirubin. This mordant also enhances the molar absorptivity of bilirubin and causes a spectral shift in the unconjugated moiety making possible the simultaneous analysis of both conjugated and unconjugated bilirubin by reading reflectance density at 400 and 460 nm.

In addition to the spectral enhancement properties of the mordant, this system. depends on the successful separation of mordanted bilirubin beneath the radiation-blocking layer and other serum pigments above the radiation-blocking layer. The mordant/reagent layer, then, must be free of pigments that absorb light in the 400 to 460 nm range of the spectrum.

The support can be any suitable dimensionally stable, and preferably, nonporous and transparent (that is, radiation transmissive) material which transmits electromagnetic radiation of a wavelength between about 200 and about 900 nm. A support of choice for a particular element should be compatible with the intended mode of detection (for example, reflectance spectroscopy). Useful supports can be prepared from polystyrene, polyesters, polycarbonates, cellulose esters and other materials known in the art.

The outermost layer is a porous spreading layer prepared from any suitable fibrous or non-fibrous material or mixtures of either or both. The term "porous" as used herein means being full of pores such that a fluid can be absorbed by capillary action and can pass to other layers in fluid contact with the porous layer. The void volume and average pore size of this zone can be varied depending upon the fluid to be tested. Useful spreading layers can be prepared using fibrous materials, either mixed with a suitable binder material or woven into a fabric, as described in U.S. Pat. No. 4,292,272 (issued Sep. 29, 1981 to Kitajima et al), polymeric compositions or particulate materials, for example, beads bound together with or without binding adhesives, as described in U.S. Pat. Nos. 3,992,158 (issued Nov. 16, 1976 to Przybylowicz et al), 4,258,001 (issued Mar. 24, 1981 to Pierce et al) and 4,430,436 (issued Feb. 7, 1984 to Koyama et al) and Japanese Patent Publication No. 57(1982)-101760. It is desirable that the spreading zone be isotropically porous, meaning that the porosity is the same in each direction in the zone as caused by interconnected spaces or pores between particles, fibers or polymeric strands.

The elements can have more than one spreading layer, each layer being prepared of the same or different materials and having the same or different porosity.

The element also comprises a radiation-blocking layer which contains a suitable radiation-blocking pigment, for example titanium dioxide or barium sulfate, distributed in a suitable hydrophilic binder material which may be the same or different from that used in the reagent layer.

The interactive mordant needed to bind with bilirubin to provide a detectable product is located in a reagent layer located beneath the radiation-blocking layer. The interactive mordants useful in the practice of this invention correspond to the mordants described in U.S. Pat. No. 4,069,017 (noted above) and the hydrophobic amines described in U.K. Patent Specification No. 2,085,581 (published Apr. 28, 1982) which are believed to become positively-charged mordants. In general, these mordants have one or more binding sites for bilirubin and comprise at least one moiety having a hydrophobic organic matrix and a charge-bearing cationic group. Such mordants can be monomeric or polymeric, but preferred mordants are homopolymers and copolymers having the properties noted above. They bind both conjugated and unconjugated forms of bilirubin.

The reagent layer also contains a hydrophilic binder material which is permeable to bilirubin. As noted above, it is preferred that the binder material not contain gelatin or a derivative of gelatin. This binder material must also be non-interfering, that is, it must not interfere with the mordanting of bilirubin to the mordant described above. In other words, it should not be capable of binding or mordanting to bilirubin.

A list of useful mordants and binder materials is described in U.S. Pat. No. 4,788,153 (issued Nov. 29, 1988 to Detwiler) which is incorporated herein by reference. The specific hydrophilic binder materials used in the present invention are described in more detail below.

Other layers, for example, subbing or filter layers, can be included in the element if desired. All of the layers in the element are generally in fluid contact with each other, meaning that fluids and nonmordanted reagents and reaction products can pass or be transported between superposed regions of adjacent layers.

The elements of the present invention are free of any interactive compositions which give a colorimetric or fluorometric response in the presence of bilirubin other than the interactive mordants described below. In particular, they are free of the diazonium salts and detectable ligands for forming detectable species known in the art for bilirubin determination, for example in U.S. Pat. Nos. 4,069,016 (issued Jan. 17, 1978 to Wu) and 4,548,905 (issued Oct. 22, 1985 to Wu).

The particularly useful binder materials of the present invention maintain the structural integrity of the element without absorbing light at 400 or 460 nm. The binder materials of the present invention comprise crosslinkable copolymers derived from:

A) one or more monomers comprising about 0 to 99, preferably 40 to 60, and most preferably about 45 to 55 weight percent of the total binder polymer, said one or more monomers being selected from the group consisting of acrylamide monomers and the monomer 1-vinyl-2-pyrrolidone. Examples of suitable acrylamide monomers include acrylamide, N-isopropylacrylamide, N-(1,1-dimethyl-3-oxobutyl)acrylamide, 2-acrylamido-2-hydroxymethyl-1,3-propanediol, N-(3-dimethylamino-propyl)acrylamide, N,N-dimethylacrylamide, N,N-diethylacrylamide, and 3-(2-dimethylaminoethyl)acrylamide. Particularly preferred is unsubstituted acrylamide; and B) one or more monomers comprising about 1 to 10, preferably about 2 to 5 weight percent of the total binder polymer, said one or more monomers having reactive groups capable of reaction with a crosslinking agent to crosslink the copolymer, and being selected from the group consisting of:

(i) primary amino group-containing monomers and the acid addition salts thereof such as N-(3-aminopropyl)methacrylamide hydrochloride, 2-aminoethyl methacrylate hydrochloride, and p-aminostyrene.

(ii) active methylene group-containing monomers, i.e., monomers having a

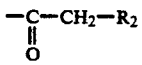

group appended thereto wherein $R_2$ is a cyano, acyl, or alkoxycarbonyl group. Suitable examples of acrylic ester monomers containing such groups include 2-acetoacetoxyethyl acrylate, 2-acetoacetoxyethyl methacrylate, ethyl α-acetoacetoxymethyl acrylate, and 2-cyanoacetoxyethyl methacrylate (described in U.S. Pat. Nos. 3,459,790 and 3,554,987). Vinyl monomers containing such groups, for example, ethyl acryloylacetate, 6-(m- and p- vinylphenyl)-2,4-hexanedione (60:40); ethyl 5-(m- and p- vinylphenyl)-3-oxopentanoate (60:40) and the corresponding methyl ester are described in U.S. Pat. Nos. 3,929,482; 3,939,130, and 3,904,418. Amide monomers containing such active methylene groups, such as N-(2-acetoacetoxyethyl)acrylamide, N-(2-acetoacetamidoethyl)-methacrylamide, 4-acetoacetyl-1-methacryloylpiperazine, acetoacetamidoethyl methacrylate, and N-(3-acetoacetamidopropyl)methacrylamide are described in U.S. Pat. Nos. 4,247,673 and 4,215,195;

(iii) activated halogen group-containing monomers which have appended halomethylaryl, halomethylcarbonyl, halomethylsulfonyl, haloethylcarbonyl, and haloethylsulfonyl groups which will, after polymerization, also undergo crosslinking with a suitable crosslinking agent such as a diamine, dithiol, diol, etc. Monomers having such halomethylaryl groups, for example, vinylbenzyl chloride, and vinylbenzyl bromide are disclosed in U.S. Pat. No. 4,017,442. Useful monomers having appended haloethylsulfonyl groups such as m- and p-(2-chloroethylsulfonylmethyl)styrene and N-(4-chloroethylsulfonylmethylphenyl)acrylamide are described in U.S. Pat. Nos. 4,161,407 and 4,548,870. Monomers which provide halomethylcarbonyl crosslinkable groups include vinyl chloracetate, N-(3-chloroacetamidopropyl) methacrylamide, 2-chloroacetamidoethyl methacrylate, 4-chloracetamidostyrene, m- and p-chloracetamidomethylstyrene, N-(3-chloroacetamidocarbonyliminopropyl)-methacrylamide, 2-chloroacetamidocarbonyliminoethylmethacrylate, 4-chloracetamidocarbonyliminostyrene, m- and p-chloracetamidocarbonyliminomethylstyrene, N-vinyl-N'-(3-chloropropionyl)urea, 4-(3-chloropropionamido)styrene, 4-(3-chloropropionamidocarbonylimino)styrene, 2-(3-chloropropionamido)ethyl methacrylate, and N-[2-(3-chloropropionamido)ethyl]methacrylamide.

It is well known that the haloethylsulfonyl and haloethylcarbonyl groups of polymers derived from monomers containing such groups can be readily dehydrohalogenated to vinylsulfonyl and vinylcarbonyl groups which are also readily crosslinkable with amine and sulfhydryl groups containing crosslinking agents in accordance with this invention, and such derived polymers are also within the scope of useful polymers of the present invention.

Polymers having active methylene or primary amine groups are conveniently crosslinked with conventional gelatin hardeners such as formaldehyde, glyoxal and dialdehydes such as succinaldehyde and glutaraldehyde as described in U.S. Pat. No. 3,232,764; active esters such as described in U.S. Pat. No. 3,542,558; active halogen compounds such as described in U.S. Pat. Nos. 3,106,468 and 3,957,882; s-triazines such as described in U.S. Pat. No. 3,325,287; aziridines such as described in U.S. Pat. No. 3,575,705; active olefins such as described in U.S. Pat. No. 3,490,911 and 3,640,720; vinylsulfones such as a bis(vinylsulfonylmethyl)ether and bis(vinylsulfonyl)methane as described in U.S. Pat. No. 3,841,872 and U.S. Pat. No. 3,539,644; halogen-substituted aldehyde acids such as mucochloric and mucobromic acids; and polymeric hardeners such as dialdehyde starches; poly(acrolein-co-methacrylic acid); poly(acrylamide-co-2-chloroethylsulfonylmethylstyrene) and poly(acrylamideco-vinylsulfonylmethylstyrene).

Polymers having activated halogen can be crosslinked with agents having two or more amino or mercapto groups such as ethylenediamine, 1,3-propanediamine, 1,3-propanedithiol, dithiothreitol, dithioerythritol, and butylenediamine.

More specifically, the polymers of this invention are those which conform to the structure:

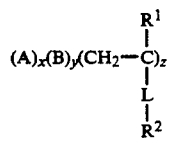

wherein:

(A) represents recurring units of one or more polymerized acrylamide monomers of the type described above;

(B) represents recurring units of polymerized 1-vinyl-2-pyrrolidone;

$R^1$ is hydrogen or methyl;

L is a linking group which is at least one, and preferably a combination of at least two, of the types of groups selected from alkylene of 1 to 30, preferably 1 to 10, carbon atoms; arylene groups of 6 to 12 ring carbon atoms, such as phenylene, tolylene, xylylene and naphthylene, —Z—, and

where alkylene means straight and branched chain alkylene and alkylene interrupted or terminated with heteroatoms or heteroatom-containing groups such as oxy, thio, imino

where $R^3$ is hydrogen or alkyl of 1 to 6 carbon atoms), ester (—COO—), amide (—CONH—), ureylene (—NHCONH—), sulfonyl (—SO₂—), and urethane (—NHCOO—) groups;

Z is 0, imino

as defined above) or an N,N'-heterocyclylene group of 5 to 7 carbon and hetero ring atoms such as 1,4-piperazinylene;

$R^2$ is a reactive group selected from the group consisting of:
  i) primary amino and acid addition salts thereof, i.e., —$NH_2$ and —$NH_2 \cdot HX$ where X is an acid anion such as halide, e.g., chloride, bromide, fluoride, and iodide;
  ii) an active methylene group, i.e., a group having an acid hydrogen atom that is easily displaced by a nucleophile, preferably conforming to the structure

—$CCH_2R4$ where $R^4$ is cyano, acyl of about 1 to 6 carbon atoms such as acetyl, propionyl, buryryl, etc., preferably acetyl, or an ester group

—$COR^5$ where $R^5$ is an alkyl group of about 1 to 5 carbon atoms; and group selected
  iii) an activated halogen group selected from halonethylaryl such as chloromethylphenyl, halomethylcarbonyl such as chloroacetyl, haloethylcarbonyl such as 3-chloropropionyl, and haloethylsulfonyl such as 2-chloroethylsulfonyl, said activated halogen groups preferably conforming to the structure:

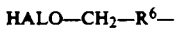
HALO—$CH_2$—$R^6$— where HALO represents a halogen atom, preferably chloro or bromo and —$R^6$— is carbonyl, an ester (—COO—), amide

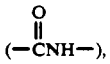
(—CNH—), methylenecarbonyl, or methylenesulfonyl group, or a sovalent bond linking the HALO—$CH_2$ group directly to the aromatic ring of an arylene group in the linking chain, e.g., to a phenylene, tolylene, xylylene, or naphthylene group in the linking chain, and x, y, and z represent weight percents, totalling 100, of the recurring units such that x is about 0 to 99, preferably 40 to 60, and most preferably 45 to 55, y is about 0 to 99, preferably 40 to 60, and most preferably 45 to 55, and z is 1 to 10, preferably 2 to 5 weight percent.

Preparation of the polymers of the invention proceeds via conventional addition polymerization techniques such as by using redox initiator systems, such as persulfate-bisulfite or hydrogen peroxide, or organic soluble free-radical-generating initiating systems such as 2,2'-azobis(2-methylpropionitrile). We prefer to use a hydrogen peroxide initiator in a conventional solution polymerization process, preferably using a mixture of water and isopropanol as the solvent.

The amount of hydrophilic binder material in the mordant layer should be sufficient to adequately disperse the mordant therein and to form a suitable film. The amount will also depend upon the type of polymeric mordant used. Where the mordant is a film-forming polymer, less binder material may be needed. Generally, the amount of binder is from about 2 to about 20 g/m² with amounts of from about 5 to about 20 g/m² being preferred.

Other optional addenda (including buffers, surfactants and the like) can be added to one or more layers of the element, if desired. Also useful in the element are one or more bilirubin effectors, or promotors as they are also known in the art. Such materials include sodium benzoate, caffeine, gum arabic, salicylate, bile salts and mixtures thereof. Preferably, such materials are included in the porous spreading layer of the elements.

A variety of different elements, depending on the method of assay, can be prepared in accordance with the present invention. Elements can be configured in a variety of forms, including elongated tapes of any desired width, sheets, slides or chips. Generally, the elements are individual slides which are packaged together in cartridges for use in automated analyzers.

The assay of this invention can be manual or automated. In general, in using the dry elements, bilirubin determination is made by taking the element from a supply roll, chip packet or other source and physically contacting it with a sample (for example up to 200 μl) of the liquid to be tested so that the sample and reagents (that is, the interactive mordant) within the element become mixed. Such contact can be accomplished in any suitable manner, for example, by dipping or immersing the element into the liquid or, preferably, by spotting the element by hand or machine with a drop of the liquid with a suitable dispensing means.

After liquid application, the element can be exposed to conditioning, such as incubation, heating or the like, that may be desirable to quicken or otherwise facilitate obtaining any test result.

When the mordant binds to bilirubin, a detectable change results which is readily measured using suitable apparatus for reflection spectrophotometry. Such apparatus is well known in the art. The signal from the detectable species so measured is indicative of the amount of bilirubin in the fluid tested.

The method and elements of this invention can be used to measure either conjugated or unconjugated forms of bilirubin according to the teaching of U.S. Pat. No. 4,338,095, noted above, and which is incorporated herein by reference. Generally, this selective measurement of one or both forms of bilirubin is accomplished by contact of liquid and element as described above, and by measuring the absorption or emission spectra at two or more wavelengths and performing the appropriate calculations.

The crosslinkable copolymers used in the element of the invention are prepared as follows.

Preparation of N-(3-acetoacetamidopropyl)methyacrylamide

Triethylamine (24 g, 0.24 mole) was added dropwise at 0° C. to a solution of N-(3-aminopropyl)methacrylamide hydrochloride (40 g, 0.24 mole) and diketene (20 g, 0.24 mole) in methanol (800 ml). After addition, the temperature was maintained at 0° C. for 2 hours under stirring. Stirring was continued at 20° C. for 20 hours. The solvent was then removed. The residue was dissolved in chloroform (1 liter), washed with 5% hydrochloric acid (200 ml), washed with saturated $NaHCO_3$ (200 ml), dried over anhydrous magnesium sulfate, and filtered. Excess solvent was removed. The residue was recrystallized from benzene (500 ml) and ethyl ether (500 ml) to give N-(3-acetoacetamidopropyl)methacrylamide (melting point = 93°–94° C.) at a yield of 50%.

Preparation of N-(3-Chloroacetamidopropyl)methacrylamide

In a 3-liter 4-neck flask fitted with condenser, stirrer, and 2-dropping funnels were placed N-(3-aminopropyl)methacrylamide hydrochloride (157 g 0.88 moles) in methanol (1.2 L) and 2,6-di-tert-butyl-p-cresol (1.0 g). In one funnel was placed chloroacetyl chloride (100 g, 0.89 mole), and in funnel two was placed triethylamine (178 g, 1.76 mole). The solution was cooled to 0°–5° C. (ice-methanol), and triethylamine was added in a slow stream over 30 minutes, and the chloroacetyl chloride was added over 1 hour. After the addition, the temperature was maintained at 0° C. for 2 hours, the ice bath was removed, and stirring was continued at room temperature overnight. The solvent was removed, and to the residue was added hot ethyl acetate (500 mL). The mixture was filtered to remove triethylamine hydrochloride, then the solid was washed with hot ethyl acetate (500 mL), filtered again, the filtrate combined, and the solvent was removed on a rotary evaporator. The residue was crystallized from ethyl acetate (400 mL) by heating to dissolve, filtering to remove any solid present, and cooling to 0° C. to crystallize. The crude monomer was purified by chromatography on a silica gel packed column. The product was eluted from the column using a 1:1 mixture of ethyl acetate and dichloromethane (4 L). The collected solvent was evaporated, and the residue crystallized from ethyl acetate (300 mL) with 2,6-ditert-butyl-p-cresol (500 mg) to give a white crystalline compound, mp 85°–90° C., 83 g (43% yield). Analysis Calculated $C_9H_{15}ClN_2O_2$: C, 49.4; H, 6.9; N, 12.8; Cl, 16.2. Found: C, 49.0; H, 7.6; N, 13.2; Cl, 17.3.

Preparation of Poly[acrylamide-co-N-vinyl-2-pyrrolidinone-co-N-(3-acetoacetamidopropyl)methacrylamide] (Weight ratio 48.75/48.75/2.5)

To a solution of acrylamide (105.3 g, 1.4 moles), N-vinyl-2-pyrrolidinone (105.3 g, 0.94 mole), N-(3-acetoacetamidopropyl)methacrylamide (5.4 g, 0.024 mole), and hydrogen peroxide (8.0 g, 30% in water) in $H_2O$ (1.8 L) and isopropanol (400 mL) which had been #10 degassed with nitrogen was heated at 65°–70°0 C. under a nitrogen atmosphere for 5 hours and allowed to sit at temperature overnight. The next day the solution was concentrated at low heat (40°–50° C.) on a rotary evaporator to about 1 L (20.5% solids). This solution was used directly for coating.

Preparation of Poly[acrylamide-co-N-vinylpyrrolidinone-co-N-(3-aminopropyl)methacrylamide Hydrochloride] (Weight ratio 48.75/48.75/2.5)

This material was prepared in the same manner as Example 3 except the polymer was precipitated in acetone (5 gal), filtered, dried in a vacuum oven and redissolved in $H_2O$ at 17.4% solids. Also, N-(3-aminopropyl)methacrylamide hydrochloride was used instead of N-(3-acetoacetamidopropyl)methacrylamide.

Preparation of Poly[acrylamide-co-N-vinylpyrrolidone-co-N-3-chloroacetamidopropyl)methacrylamide] (Weight ratio 48.75/48.75/2.5)

This material was prepared in the same manner as Example 4 except that N-(3-chloroacetamidopropyl)methacrylamide was used instead of N-(3-aminopropyl)methacrylamide hydrochloride.

EXAMPLE 1

Comparison of Elements with Different Binder Materials in Reagent Layer

This is a comparison between the element of the present invention and two control elements. The two control elements were prepared in the same manner as the element of the present invention except that one had hardened gelatin as the binder material in the reagent layer, and the other had poly(acrylamide-co-N-vinyl-2-pyrrolidone) (Weight ratio 50/50).

The element of the present invention had the format and components illustrated below. The term "dry" used herein to describe the weight of the components indicates that the coating coverage is determined as dry weight after normal coating and drying processes.

TABLE I

| | Coating Format | | |
|---|---|---|---|
| | Dry G/m² | | Useful Ranges G/m² |
| Spreading Layer | 61.388 | Anatase TiO₂ | 10–200 |
| | 10.293 | Cellulose Acetate | 50–600 |
| | 2.027 | Triton X-405 | 0–20 |
| | 1.015 | Brij 78 | 0–20 |
| | 5.614 | Caffeine | 0.5–10 |
| | 5.293 | Sodium Benzoate | 0.5–10 |
| | 2.321 | Polyurethane | 0–50 |
| Sub Layer | 0.390 | Poly-N-Isopropylacrylamide | 0.5–5 |
| Radiation | 21.770 | Anatase TiO₂ | 5–50 |
| Blocking Layer | 0.002 | Ottasept | 0–.05 |
| | 1.915 | Gel | 0.2–5 |
| | 0.153 | Surfactant Olin 10G | 0.01–1 |
| | 0.127 | Daxad | 0.01–1 |
| Reagent Layer | 8.781 | Binder (Polymer i, ii, or iii) | 3–15 |
| | 0.003 | Ottasept | 0–0.05 |
| | 1.758 | Mordant | 0.2–5 |
| | 3.619 | Bicine | 0.5–5 |
| | 0.138 | Surfactant 10G | 0.01–1 |
| | 0.110 | Crosslinking agent | 0.01–0.5 |

KEY:
Polymer i is Poly(acrylamide-co-N-vinylpyrrolidone -co-N-(3-aminopropyl)methacrylamide Hydrochloride)
Polymer ii is Poly(acrylamide-co-N-vinyl-2-pyrrolidone-co-N-(3-acetoacetamidopropyl)methacrylamide)
Polymer iii is Poly(acrylamide-co-N-vinyl pyrrolidone -co-N-(3-chloroacetamidopropyl)methacrylamide)
Triton X-405 is an octylphenoxy polyethoxy ethanol surfactant sold by Rohm and Haas Co. (rights purchased by Union Carbide Co.)
Brij 78 is a polyoxyethylene stearyl ether surfactant sold by ICI Americas Inc.
Estane is a polyester-polyurethane sold by B. F. Goodrich.
Ottasept is a bactericidal agent.
Gel is deionized gelatin.
Surfactant 10G is a nonylphenoxypolyglycidol sold by Olin Chem. Co.
Daxad is the sodium salt of a carboxylic acid polymeric surfactant/dispersing agent sold by W. R. Grace.
Mordant is a cationic polymer mordant of the type described in U.S. Pat. 4,338,095.
Bicine is N,N-bis(2-hydroxyethyl)glycine buffer.

The effectiveness of the binder materials in the regent layers of five different elements were evaluated as follows. A pool of neonate serum was divided into five pools and spiked with 0, 50, 100, 200 and 300 mg/dL of hemoglobin int he form of a hemolysate. The spiked pools were then run and Bu and Bc predictions obtained. Slides to be tested were calibrated on a KODAK EKTACHEM analyzer using standard calibrators. The changes in predicted Bu and Bc concentrations were tabulated as a function of hemoglobin concentration.

Table II illustrates the results for the five types of elements tested.

TABLE II

| Changes in Predicted Concentration Due to Addition of Hemoglobin: All Values are in mg/dL | | | | | | | | |
|---|---|---|---|---|---|---|---|---|
| | Bc | | | | Bu | | | |
| Hemoglobin Added: | 50 | 100 | 200 | 300 | 50 | 100 | 200 | 300 |
| Standard Formula poly[acrylamide-co-N-vinyl-2-pyrrolidone] | 0.41 | 0.76 | 1.54 | 2.11 | −0.34 | −0.59 | −1.17 | −1.45 |
| Hardened Gel | 0.28 | 0.55 | 1.08 | 1.44 | −0.18 | −0.32 | −0.63 | −0.79 |
| Polymer i | 0.36 | 0.55 | 1.25 | 1.59 | −0.22 | −0.40 | −0.78 | −0.99 |
| Polymer ii | 0.18 | 0.32 | 0.60 | 0.78 | −0.16 | −0.21 | −0.39 | −0.48 |
| Polymer iii | 0.27 | 0.50 | 1.02 | 1.35 | −0.19 | −0.29 | −0.64 | −0.80 |

Polymer iii was crosslinked with dithiothreitol(DTT). The other binders were crosslinked with Bis(Vinylsulfonylmethyl ether (BVSME).

The above results show that all of the crosslinkable binders (gelatin and polymers i, ii, and iii) show less change due to hemoglobin. In particular, polymer ii shows the least change. Thus, these polymers and gelatin are less sensitive to interference by hemoglobin. These polymers are hydrolytically stable and thus the crosslinking is expected to remain intact and maintain coating integrity.

The invention has been described in detail with particular reference to preferred embodiments thereof, but it will be understood that variations and modifications can be effected within the spirit and scope of the invention.

We claim:

1. An analytical element for the determination of conjugated or unconjugated bilirubin comprising a support having thereon, in order from said support.
   (A) a reagent layer comprising a positively-charged interactive mordant for bilirubin, said mordant being dispersed in a copolymer binder material derived from:
      (1) one or more monomers selected from the group consisting of acrylamide and N-vinylpyrrolidone; and
      (2) one or more crosslinkable monomers selected from the group consisting of (i) primary amino group-containing monomers, and (ii) activated halogen group-containing monomers;
   (B) a radiation blocking layer; and
   (C) a porous spreading layer.

2. The analytical element of claim 1 wherein the binder material in the reagent layer is poly[acrylamide-co-N-vinylpyrrolidone-co-N-(-b 3-aminopropyl)methacrylamide hydrochloride].

3. The analytical element of claim 1 wherein the binder material in the reagent layer is poly[acrylamide-co-N-vinylpyrrolidone-co-N-(-b 3-chloroacetamidopropyl)methacryl-amide].

4. The element of claim 1 wherein the radiation blocking layer comprises inorganic pigment particles dispersed in a binder material similar to the binder material in the reagent layer.

5. The element of claim 1 wherein the radiation blocking layer comprises inorganic pigment particles dispersed in a binder material other than the binder material in the reagent layer.

6. An analytical element for the determination of conjugated or unconjugated bilirubin comprising a support having thereon, in order from said support:
   (A) a reagent layer comprising a positively-charged interactive mordant for bilirubin, said mordant being dispersed in poly[acrylamide-co-N-vinylpyrrolidone-co-N-(3-acetoacetamidopropyl)methacrylamide];
   (B) a radiation blocking layer; and
   (C) a porous spreading layer.

7. A method for the determination of conjugated or unconjugated bilirubin in a sample liquid comprising the steps of:
   (A) contacting an aqueous sample liquid with the analytical element of claim 1, 3, or 6; and
   (B) measuring the amount of conjugated or unconjugated bilirubin bound to said interactive mordant.

8. The method of claim 7 wherein conjugated and unconjugated bilirubin bound to the interactive mordant are measured by reading reflectance densities at more than one wavelength.

* * * * *

UNITED STATES PATENT AND TRADEMARK OFFICE
CERTIFICATE OF CORRECTION

PATENT NO. : 5,286,450
DATED : February 15, 1994
INVENTOR(S) : Hasselberg, et al It is certified that error appears in the above-indentified patent and that said Letters Patent is hereby corrected as shown below:

```
Column 2, line 14, delete "pyrrolidinone" and insert
--pyrrolidone--.
Column 12, line 3, delete "int he" and insert --in the--.
Column 12, line 4, delete "-b".
Column 12, line 12, delete "-b".
```

Signed and Sealed this

Second Day of August, 1994

Attest:

BRUCE LEHMAN

*Attesting Officer*　　　　　*Commissioner of Patents and Trademarks*